United States Patent [19]

Wertz et al.

[11] Patent Number: 5,047,072
[45] Date of Patent: * Sep. 10, 1991

[54] ULTRAVIOLET AIR ENHANCEMENT AND LASER PLUME EVACUATION METHOD AND SYSTEM

[75] Inventors: Thomas J. Wertz, The Woodlands; Gerald D. Abell, Spring, both of Tex.; Russell W. Todd, Silver Spring, Md.

[73] Assignee: Surgical Laser Products, Inc., The Woodlands, Tex.

[ * ] Notice: The portion of the term of this patent subsequent to Jan. 22, 2008 has been disclaimed.

[21] Appl. No.: 495,569

[22] Filed: Mar. 19, 1990

Related U.S. Application Data

[63] Continuation-in-part of Ser. No. 269,629, Nov. 10, 1988, Pat. No. 4,986,839.

[51] Int. Cl.$^5$ .............................................. B01D 46/00
[52] U.S. Cl. .......................................... 55/1; 55/274; 55/279; 55/316; 55/387; 422/24; 422/121; 604/19; 604/20; 604/313; 604/319
[58] Field of Search ...................... 55/279, 1, 274, 316, 55/387; 604/268.19, 313, 20, 319, 320; 422/24, 121

[56] References Cited

U.S. PATENT DOCUMENTS

| | | | |
|---|---|---|---|
| 1,789,262 | 1/1931 | Monro et al. | 183/47 |
| 2,505,173 | 4/1950 | Conley | 128/141 |
| 3,012,322 | 12/1961 | Thompson | 32/33 |
| 3,308,609 | 3/1967 | McCulloch et al. | 55/472 |
| 3,680,560 | 8/1972 | Pannier, Jr. et al. | 128/276 |
| 3,804,942 | 4/1974 | Kato et al. | 55/316 |
| 3,812,370 | 5/1974 | LaViolette | 55/316 |
| 3,843,865 | 10/1974 | Nath | 219/121 L |
| 3,889,657 | 6/1975 | Baumgarten | 128/2 B |
| 3,910,276 | 10/1975 | Polanyi et al. | 128/303.1 |
| 3,982,541 | 9/1976 | L'Esperance, Jr. | 128/303.1 |
| 4,143,660 | 3/1979 | Malyshev et al. | 128/303.1 |
| 4,182,385 | 1/1980 | Williamson | 141/65 |
| 4,266,549 | 5/1981 | Kimura | 128/303.1 |
| 4,487,606 | 12/1984 | Leviton et al. | 604/319 |
| 4,496,378 | 1/1985 | Kish | 55/316 |
| 4,516,973 | 5/1985 | Telang | 604/319 |
| 4,619,672 | 10/1986 | Robertson | 55/316 |
| 4,810,269 | 3/1989 | Stackhouse et al. | 55/319 |
| 4,826,513 | 5/1989 | Stackhouse et al. | 55/316 |
| 4,906,261 | 3/1990 | Mohajer | 55/279 |

OTHER PUBLICATIONS

U.S. Ser. No. 286,002 filed May, 1943, Eckhardt.

Primary Examiner—Bernard Nozick
Attorney, Agent, or Firm—Workman, Nydegger & Jensen

[57] ABSTRACT

In a single portable housing a system for evacuating a laser plume from a surgical site. The system extracts the laser plume from the surgery site through a primary inlet tube supported on an articulated arm. A suction canister communicating with the primary inlet tube removes liquid contaminants from the laser plume and is connected by a secondary inlet tube to a primary filter canister in which is located a primary filter comprised of activated carbon granules. Also disposed in the primary filter canister upstream on the pathway followed by the laser plume through the system is a disposable prefilter disc. In combination with the primary filter the prefilter disc removes substantially all of the particulate contaminants and odor in the laser plume. Downstream from the primary filter canister is a fan for advancing the laser plume through the system. The fan blades of the fan are enclosed in a fan housing having an inner surface taking the form of a spiral in a plane normal to the rotational axis of the fan blade. From the fan the laser plume enters a sterilization chamber containing an ultraviolet light source where all remaining biologically viable contaminants are killed. A secondary filter containing a vertically disposed pleated filter and a layer of activated carbon granules receives the output from the sterilization chamber.

49 Claims, 9 Drawing Sheets

ULTRAVIOLET AIR ENHANCEMENT AND LASER PLUME EVACUATION METHOD AND SYSTEM

RELATED APPLICATIONS

This is a continuation-in-part application of U.S. patent application Ser. No. 269,629 filed on Nov. 10, 1988, now U.S. Pat. No. 4,986,839.

BACKGROUND

1. Field of the Invention

This invention relates to systems for protecting health and safety of medical personnel during laser surgery. More particularly, the present invention is directed to a self-contained air enhancement system for evacuating and processing the laser plume created by the laser surgery.

2. Background Art

The use of lasers in surgery has rapidly expanded in recent years. Initially, lasers were found to be particularly useful in very delicate precision surgery. As a result, laser eye surgery and other types of microsurgery became well accepted during the 1970's. Indeed, many laser surgical devices incorporated a microscope into a laser source so that the area on which surgery was performed could be adequately and accurately viewed.

Since the introduction of lasers into surgical procedures, lasers have found utility in areas outside of microsurgery. For example, lasers have currently found wide acceptance in gynecological surgery.

With the rapid expansion in the use of lasers as surgical instruments, new problems have been encountered which have not been confronted in conventional surgery. One such problem is that of the smoke or laser plume produced during laser surgery. While some smoke may be produced by conventional electric scalpels and similar devices, the intensity and volume of the smoke and pollutants produced in laser surgery presents a problem of much larger magnitude.

The high intensity of lasers used in laser surgery causes oxidation of tissue and fluid contacted by the laser. This typically results in a dense laser plume emitted from the surgical site. The laser plume contains a variety of hydrocarbon compounds, carbon monoxide, moisture, and unpleasant odors. It is also now conjectured that the laser plume may contain quantities of biologically viable material, which could range in content from relatively benign organisms to cancerous and deadly viral materials.

In one study which sought to determine the scope and intensity of the smoke produced during surgery, tissue was contacted by a laser under controlled conditions. It was found that the smoke and particulate matter produced amounted to almost 7.9 milligrams per cubic meter. This smoke density is approximately 52 times greater than the recommended density set by the governmental regulatory agencies.

In addition, the laser plume is known to contain particles of varying sizes. For example, one investigation found particles varying in size from under 0.4 microns to over 9.0 microns. Nevertheless, a large portion of the particles found in that study were under 1.1 microns in size which are capable of being easily deposited in the alveoli of the lungs. Not only are particles of this size irritating to the respiratory system, but they may also be capable of causing serious respiratory disease. Repeated exposure to such particles can build deposits within the lungs.

Several investigators have pointed out that repeated exposure to laser plumes may, for example result in pneumonitis. In addition, it has been found that the laser plume may be mutagenic, and thus possibly carcinogenic. The presence of biological viable materials poses the risk of the spread of contagions. While much of the data in this area is still not definitive, it is clear that direct contact with laser plumes presents significant health risks, particularly to exposed medical personnel and patients.

Laser plumes present additional difficulties. For example, it has been found that the laser plumes condense on the optical components of the laser itself, thereby impairing visibility or causing pitting damage to lenses. Similarly, the laser plume may enter and clog mechanical devices and filters located in the operating room.

In order to combat the problems of damage to the laser itself, many conventional laser systems are equipped with air circulation systems. These systems drive a stream of air over the sensitive laser equipment and the area being contacted by the laser beam. While the laser plume is thus driven away from the laser equipment, it is forced into the ambient air, making it more difficult to control laser plume emissions.

Also, the superheated steam component of the laser plume may cause serious burns in the event of contact with the flesh. Of course, the primary danger in this regard is to the patient. The steam is produced by vaporizing irrigation or body fluids, and there is a danger that those vaporized fluids may contact the surrounding tissue.

When the steam does leave the localized surgical site, there is a danger that the heat may cause discomfort or otherwise provide an undesirable distraction to the surgeon or other operating room personnel. Thus, it is important that the steam produced in laser surgery be controlled and removed from the surgical site before it injures the tissues surrounding the surgical site or becomes a problem to operating room personnel.

Good practice thus dictates that the laser plume be controlled and removed from the surgical site, and various devices have been developed for this purpose. Most involve the use of some form of suction.

The initial attempts to remove the laser plume simply used the vacuum system built in to the operating room. This solution, however, proved to be unsatisfactory because such vacuum systems are not equipped to handle the dense hydrocarbon saturated smoke and associated moisture contained within the laser plume. Untreated laser plumes have been found to be capable of clogging and completely disabling an entire built-in hospital vacuum system.

Laser surgery often requires intense concentration on the part of the surgeon and other assisting medical personnel. It is desirable to keep machinery and distractive noise in the operating room to a minimum. A significant disadvantage of the use of a portable vacuum system is the undesirable noise it introduces into the operating room. Portable systems have limited filter capacity. There filters become easily clogged with the particulate debris and other matter, rendering them ineffective.

Clogged filters cause resistance to air flow through the system, causing inefficient laser plume removal. Filters of conventional systems must thus be replaced quite often to ensure that suction levels are adequate for removing the laser plume from the surgical site. This results in increased maintenance costs, as well as in disruptions to the surgical procedure.

Studies have been performed concerning various methods for removing laser plumes. It has been found that if a suction device having appropriate air flow rates can be placed within approximately 1 centimeter of the source of the laser plume, then over 98% of the smoke and debris will be removed before entering the ambient air. If the suction source with the same air flow is placed 2 centimeters from the source, however, only slightly over 50% of the smoke in the plume is removed. Thus, in the setting of the surgical theatre, it is important that laser plume removal systems be flexible and maneuverable, not bulky and hard to handle.

BRIEF SUMMARY AND OBJECTS OF THE INVENTION

One object of the present invention is to provide an effective and efficient system for removing the laser plume from the site of laser surgery.

It is an additional object of the present invention to provide a self-contained system as described above which is further capable of filtering and sterilizing the laser plume into clean, deodorized air.

Yet another object of the present invention is to provide a laser plume evacuation system which is simple to operate and which employs filters that are inexpensive to manufacture and that are capable of being produced in either a disposable or a reusable form.

An additional object of the present invention is to provide a laser plume evacuation system which is capable of generating increased air flow rates, while maintaining noise levels below those found in prior art systems.

It is a further object of the present invention to provide a laser plume evacuation system which uses inexpensive, but effective, filters and which is configured so that the filters may be easily and conveniently replaced.

It is another object of the present invention to provide a laser plume evacuation system which is self-contained and does not rely on a hospital vacuum system, thereby eliminating the risk that the hospital vacuum system does not provide sufficient suction for the needs of the laser surgeon.

Yet another object of the present invention is a laser plume evacuation system as described above that reduces to a minimum the possible escape from the surgical site of biologically viable materials.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, a self-contained air enhancement system is provided for removing contaminants from a laser plume produced by a laser at a surgical site. In one embodiment, the inventive system comprises a housing, a primary inlet tube for extracting the laser plume from the surgical site, and a suction canister in communication with the inlet tube for removing liquid components of the contaminants from the laser plume. A primary filter canister is located in the housing in communicating with the suction canister through a secondary inlet tube. The primary filter canister houses a prefilter disc and a primary filter for removing substantially all of the particulate contaminants and the odor from the laser plume. The primary filter comprises a body of activated charcoal disposed adjacent to the prefilter disc downstream therefrom on the pathway of the plume through the system. In some embodiments, the suction canister and secondary inlet tube are bypassed, and the primary inlet tube is connected directly to the primary filter canister.

In one aspect of the present invention, suction means are located downstream from the primary filter on the pathway of the laser plume through the inventive system. The suction means draws the laser plume in sequence through the primary inlet tube, the suction canister, the secondary inlet tube, and the primary filter canister. In one embodiment of the present invention, the suction means comprises a fan blade and an electric motor for driving the fan blade in rotation. The isolation means comprises a fan housing surrounding the fan blade for containing the laser plume.

The suction means of the present invention is facilitated by a ventilation means for supplying cooling air at ambient temperature to the suction means and isolation means for preventing cross-contamination of the cooling air by the laser plume as the laser plume passes through the housing of the system. Enhanced air flow characteristics and reduced noise have been observed when interior of the fan housing assumes a spiral configuration in a plane normal to the axis of the fan blade.

In one aspect of the present invention, sterilization means are provided for killing biologically active material in the laser plume. Briefly stated, the sterilization means comprises a source of ultraviolet light disposed along the pathway of the laser plume through the inventive system. In one embodiment, the sterilization means comprises a sterilization chamber located along the pathway of the laser plume and a baffle so disposed in the sterilization chamber as to cause the laser plume to travel in a serpentine path therethrough One or more ultraviolet light tubes are disposed along the serpentine path so as to emit ultraviolet energy in a density in the range of from about 1900 microwatts per square centimeter to about 6000 microwatts per square centimeter.

The effect of the primary filter may be enhanced by the inclusion in the system of a secondary filter located downstream from the suction means of the invention. The secondary filter comprises a vertically pleated filter having a cylindrical shape and a layer of activated charcoal disposed between the pleated filter and the suction means.

The inventive system further comprises an indicator means for alerting a user of the system that the primary filter thereof should be replaced. A pressure differential tube measures the pressure difference between ambient pressure and that generated by the suction means. An indicator means, such as a light or sound device, is provided for alerting a user when the pressure difference exceeds a predetermined threshold.

Several structural features contribute to an increased air flow from the surgical site without increasing the size of any fan used with the system. The inlet port to the suction canister can, for example, be made to have a diameter smaller than that of the outlet port. The primary inlet tube and the secondary inlet tube are provided with a smooth interior and, except at the end close to the surgery site, with a relatively large diameter in the range from about 1.00 inches to about 1.75 inches, or most preferably in the range from about 1.25 inches to about 1.345 inches. Optionally, tube reduction means may be provided for connecting a first portion of said inlet tube remote from said suction means to a second portion of said inlet tube located between said first portion thereof and said suction means, where the first portion has a smaller inner diameter than the inner diameter of the second portion of said inlet tube. This permits the end of the inlet tube close to the surgery site to be quite small, but the capacity of the system to be substantial. Conveniently, the system is foot operable and has controls capable of regulating the degree of suction produced.

The present invention also contemplates a method for the efficient removal of contaminants in a laser plume produced at a surgical site. In that method, the laser plume is aspirated from the surgical site to a single mobile unit. There liquid contaminants are removed from the laser plume and substantially all particular contaminants and odor are filtered therefrom. The laser plume is sterilized to eliminate all biologically active materials and then expelled into the atmosphere. The step of filtering the laser plume comprises the steps of advancing the laser plume through a primary charcoal filter immediately after the step of removing liquid contaminants and the step of passing the laser plume through a secondary charcoal filter immediately after the step of sterilizing the laser plume. The step of sterilizing the laser plume comprises the steps of driving the laser plume in a serpentine line of travel through a sterilization chamber and exposing the laser plume to ultraviolet radiation as the laser plume is so driven.

It will be appreciated that the current invention is simple and easy to use. Because of its efficient design, the present invention provides better filtration than systems taught in the prior art while having the capability to provide greater suction capabilities at reduced noise levels.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

The present invention can best be understood by reference to the drawings, wherein like parts are designated with like numerals throughout.

Figure 1:
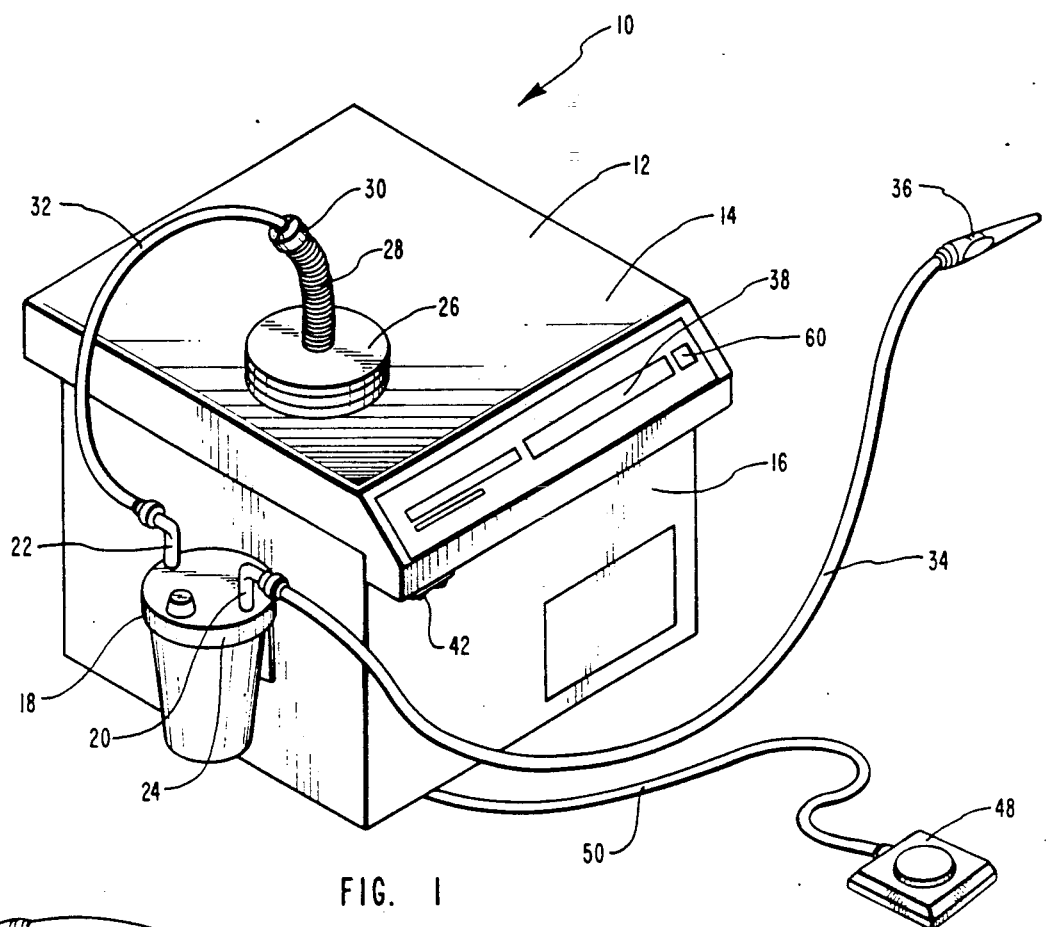
FIGS. 1 and 1A are perspective views from different viewpoints of a first embodiment of a self-contained air enhancement evacuation system incorporating teachings of the present invention.
Figure 1A:
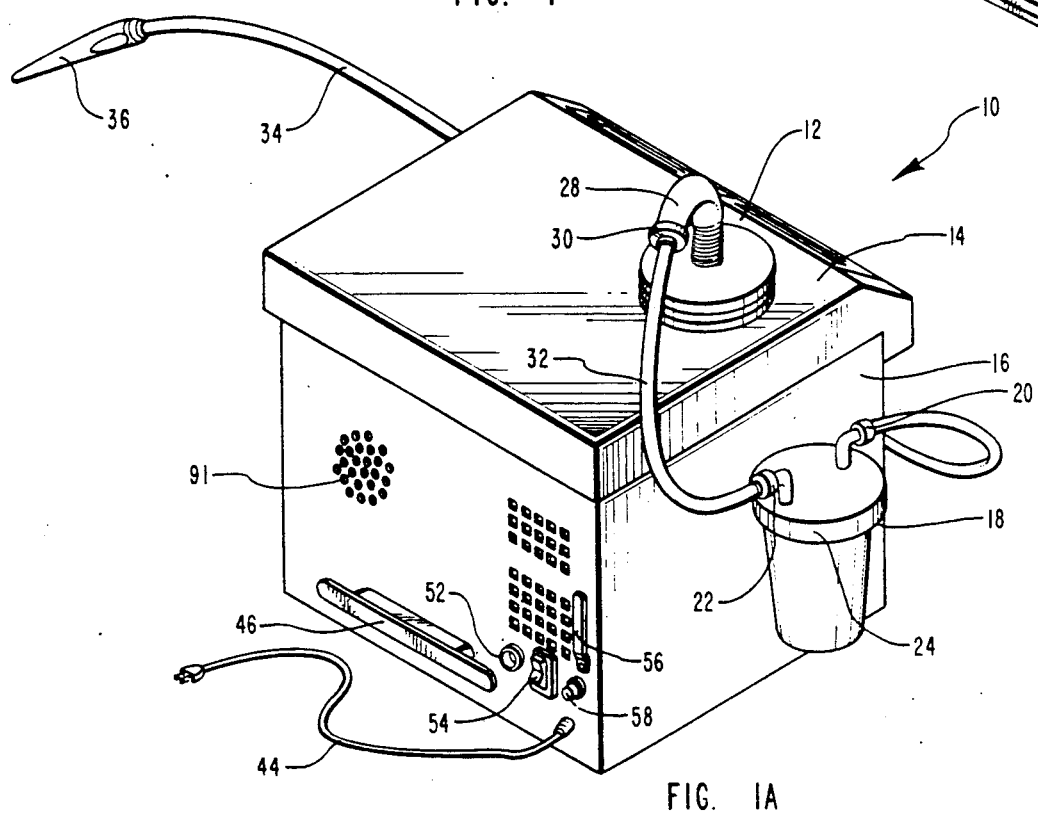

In FIGS. 1 and 1A, a first embodiment 10 of a laser plume evacuation system is illustrated. A system housing 12 is provided in which the various components of the system are housed. System housing 12 comprises a system top housing 14 and a system bottom housing 16. System housing 12 may be made out of a variety of materials. It is presently preferred that the material have a smooth finish to facilitate its cleaning by medical personnel.

A suction canister 18 is provided which removes any liquids and gross particulate matter which are aspirated from the surgical site when the present invention is used for closed surgical procedures. The suction canister has an inlet port 20 and outlet port 22 extending from it. Inlet port 20 is preferably configured to receive a ¼ inch conventional suction tubing.

Outlet port 22 is configured to receive a larger tubing, such as a ⅜ inch tubing, thereby providing greater suction capabilities at the surgical site without requiring the use of a larger motor. The suction canister is mounted to the side of the system housing by a mounting ring 24.

Still referring to FIGS. 1 and 1A, a prefilter housing top 26 is provided and configured to receive an inlet tube 28. It is presently preferred that inlet tube 28 have a large inside diameter, thereby providing for increased suction capabilities at the surgical site. In preferred embodiments of the present invention, inlet tube 28 has an inside diameter of 1.25 inches to 1.345 inches. A tube reducer 30 may be connected to the inlet tube to enable the inlet tube to be connected to a smaller diameter tube leading either to the surgical site or to the suction canister.

All of the suction tubes employed in the present invention are preferably transparent, thereby allowing the medical personnel to readily observe whether debris is accumulating at any point in the tubes. The tubes are constructed of any of the plastic compositions conventionally known in the plastics art for similar medical applications. The tubes are configured with a smooth inside surface thereby reducing any possibility that debris will build up, obstructing the flow of air through the system. Additionally, the smooth inside surface of the tubes helps reduce the noise which accompanies the flow of air through the tubes.

In the embodiment of the present invention illustrated in FIGS. 1 and 1A, a suction tube 32 is connected at one end to inlet tube 28 of a prefilter housing 26 through tube reducer 30 and at its distal end to outlet port 22 of suction canister 18. The inside diameter of suction tube 32, as illustrated in FIG. 1, is approximately ⅜ inch. A suction wand leader tube 34 is connected to inlet port 20 of suction canister 18 at one end and connected to a suction wand 36 at its opposite end. The suction wand is used to aspirate the laser plume from the surgical site.

In an alternative embodiment of the present invention, suction canister 18 is eliminated or bypassed and suction tube 32 is connected directly to the suction wand. In such an embodiment, it is preferable that a long length of inlet tube 28 (with a 1.25 inch to 1.345 diameter) be used which is connected to a short length of suction tube 32 by means of a suitable tube reducer. By maximizing the length of large-diameter tubing, the resistance in the system is minimized.

Suction wand leader tube 34 and suction wand 36 are provided in a sterile form for closed surgical procedures, thereby maintaining sterile conditions at the surgical site.

By reducing the amount of smaller diameter tubing in the system, the suction capabilities of the system are increased without the necessity of providing a larger vacuum motor. An additional advantage of this configuration is that the increased noise levels associated with larger vacuum systems are eliminated. Noise levels are also kept to a minimum by employing suction tubes having a smooth inner surface, as explained above.

A suction control panel 38 is provided in the system top housing 14 so that the controller or other medical personnel can control the amount of suction at the surgical site. In one presently preferred embodiment of the present invention, suction control panel 36 contains ten different settings which may be used to obtain air flow rates from approximately 10 cubic feet per minute to approximately 50 cubic feet per minute. It will be appreciated that the control panel may be replaced with a dial or any other suitable means for adjusting the flow of air through the system.

A power switch 42 is mounted on the system top housing whereby the medical personnel can provide power to the system. Power is supplied to the system through power cord 44, which may be stored on the system housing by wrapping it around cord wrap bracket 46.

Alternatively, a foot switch 48 may be employed to facilitate turning on the system. Foot switch 48 includes foot switch cord 50 which enters system bottom housing 16 at foot switch port 52, as viewed in FIG. 1A. The operator of the system may control whether power switch 42 or foot switch 48 actuate power to the system with bypass switch 54.

Also mounted on system housing 12 is a tube holder bracket 56 through which excess tubing, such as suction wand leader tube 34, may be placed. A circuit breaker 58, such as those commonly employed in the electrical arts, may also be mounted on system housing 12.

To enable the operator of the system to test the system prior to using the system at the surgical site, a test button 60 is provided. Test button 60 is preferably mounted adjacent suction control panel 38 and may be actuated to indicate to the operator of the system whether the filter employed in the system needs to be changed, as will be explained below in further detail.

Because of the relative compact size of the system, the system may be mounted on a typical cabinet having drawers in which may be kept accessories to the system. Advantageously, the cabinet may have casters mounted at its base to render the system portable, thereby facilitating transportation of the system into the operating room.

Figure 2:
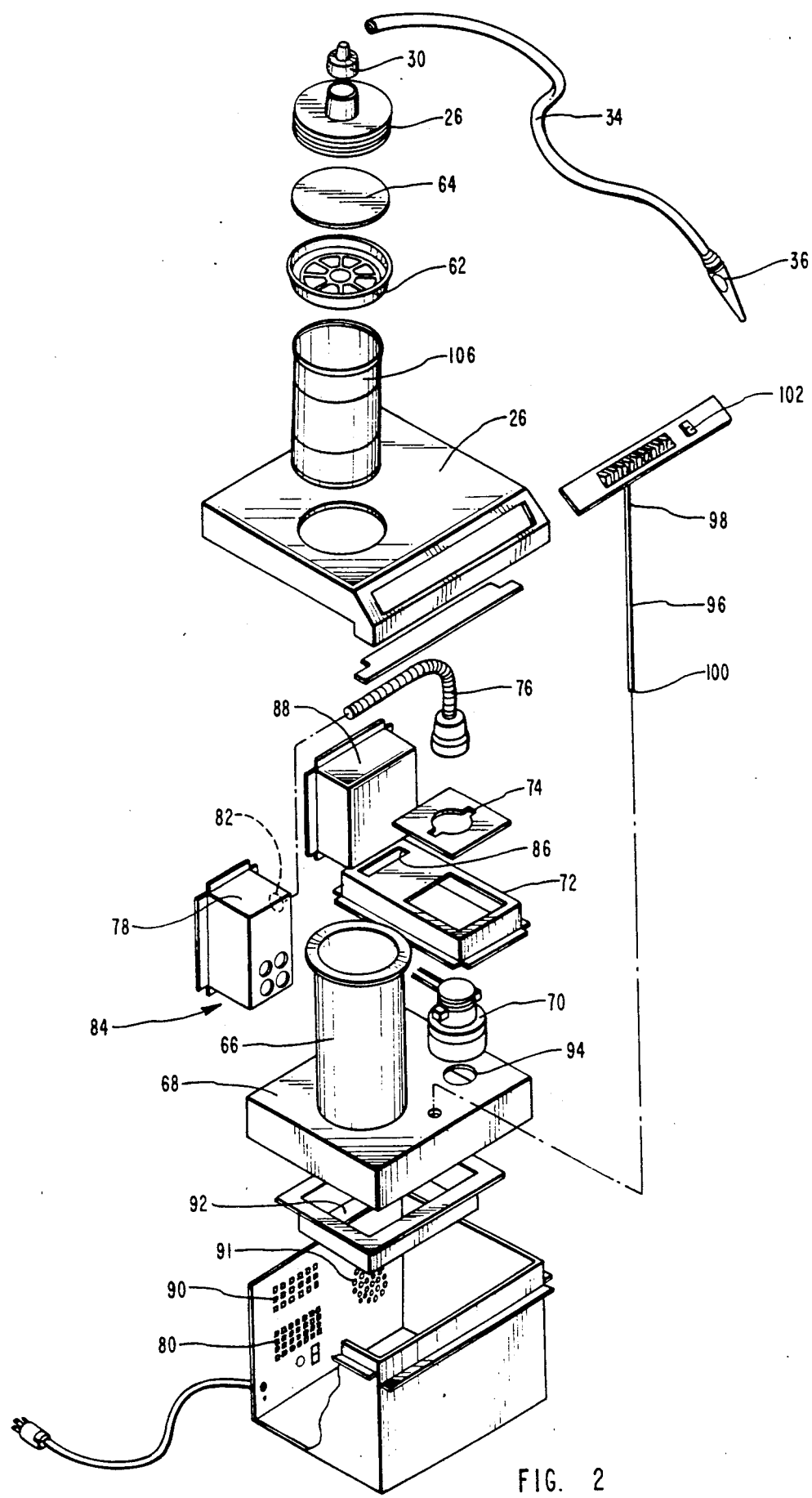
FIG. 2 is an exploded perspective view of the system shown in FIG. 1.

Referring now to FIG. 2, the various components contained within the system housing 12 are illustrated and explained. Prefilter housing top 26 is connected directly to a prefilter housing base 62. Between prefilter housing top 26 and prefilter housing base 62 is placed a prefilter disc 64, which initially removes larger particulate matter from the laser plume. The prefilter housing base 62 attaches to a filter canister 106 which may be placed into filter cylinder 66. Filter cylinder 66 is mounted to a base plate 68 within the system housing.

Also mounted to base plate 68 is a conventional vacuum motor 70. A vacuum motor retainer housing 72 is specially configured to fit over vacuum motor 70 and to be mounted to base plate 68. The vacuum motor retainer housing contains a keyed air duct 74 which fits over the vacuum motor such that the motor component of the vacuum extends above housing 72.

A cooling air supply tube 76 channels ambient air for cooling vacuum motor 70. The cooling air for vacuum motor 70 is obtained through a cooling air supply/exhaust chamber 78. It is through the cooling air supply/exhaust chamber that cool, ambient air is provided through cooling air supply tube 76 to the vacuum motor.

The cooling air supply/exhaust chamber is open to the ambient air through a cooling air vent 80 contained in the side wall of system bottom housing 16. Cooling air supply/exhaust chamber 78 is configured with an inlet duct 82 through which ambient air flows into cooling air supply tube 76 and to the vacuum motor. After the cooling air has passed over the vacuum motor and provided its cooling function, it enters cooling air supply/exhaust chamber 78 through an exhaust duct 84 where it exits into the ambient air through cooling air vent 80.

Still referring to FIG. 2, vacuum motor retainer housing 72 is also provided with a filtered air duct 86 through which filtered air may flow into a filtered air exhaust chamber 88 and exit into the ambient air through a filtered air exhaust vent 90 contained in system bottom housing 16, as will be explained below in greater detail.

The flow of aspirated air through the system may be explained with reference to FIGS. 1 and 2. The laser plume is aspirated from the surgical site through suction wand 36. are directed into suction canister 18, as illustrated in FIG. 1, where the liquids and gross particulate matter contained within the laser plume are removed. Referring now to FIG. 2, the laser plume is then directed to prefilter housing top 26 through inlet tube 28. After flowing through the prefilter, the air passes through the primary filter, located within filter cylinder 66, where the toxic elements are removed from the air, as well as any particulate matter which may have not been removed by the prefilter.

The air then flows from the primary filter directly into a vacuum chamber 92. The vacuum motor is in direct connection with vacuum chamber 92 through an orifice 94 in base plate 68. Thus, as the vacuum motor is actuated, the resulting suction through orifice 94 causes reduced pressure in vacuum chamber 92 relative to the ambient pressure. The air which has now passed through the primary filter exits vacuum chamber 92 through orifice 94 where drawn to the fans rotated by vacuum motor and is then expelled from vacuum motor retainer housing 72 through filtered air duct 86. The filtered air duct is in direct connection with a filtered air exhaust chamber 88. Thus, as the filtered air exits the system, it flows through filtered air duct 86, into filtered air exhaust chamber 88, and is expelled into the ambient air through a filtered air exhaust vent 90 contained in the side of system bottom housing 16. The laser plume evacuation system of the present invention is thus configured such that the air provided to cool the vacuum motor is never mixed with the air being filtered through the system.

As air is filtered through the system, the primary filter becomes filled with particulate debris which causes the filter's resistance to the flow of air passing through the system to increase. To enable medical personnel to properly determine when the primary filter needs to be changed, a pressure differential tubing 96 is provided in the system which measures the pressure differential between the vacuum created in vacuum chamber 92 and the ambient air pressure. This feature may be accessed by placing the system in test mode by actuating test button 60.

As can be observed by reference to FIG. 2, pressure differential tubing 96 is mounted at its upper end 98, as viewed in FIG. 2, on the inside of suction control panel 38 where it is exposed to ambient air pressure. The bottom end 100 of pressure differential tubing 96 is mounted to base plate 68 and is exposed to vacuum chamber 92. As the primary filter begins to be clogged with debris and the resistance to the passage of air through the filter increases, the pressure differential between the ambient air and the pressure within vacuum chamber 92 also increases.

Figure 3:
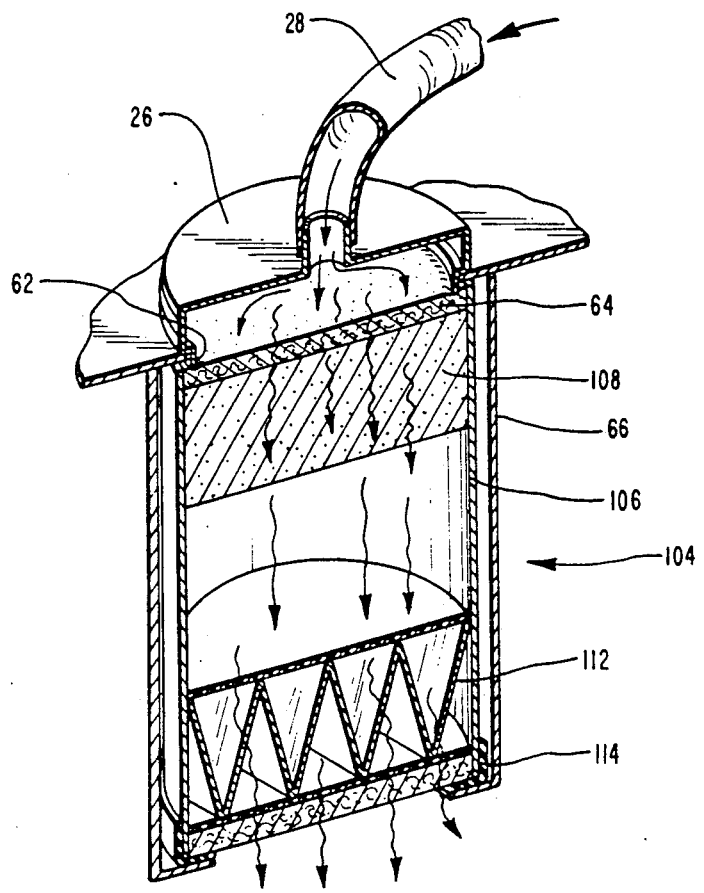
FIG. 3 is a cross-sectional perspective view of one embodiment of a primary filter employed in the system shown in FIG. 1.

A first embodiment of a primary filter 104 of the present invention is illustrated in FIG. 3. Inlet tube 28 is connected directly to prefilter housing top 26. In the embodiment of the present invention illustrated in FIG. 3, prefilter housing top 26 may be repeatedly used if cleaned after each use.

The prefilter housing top is preferably connected to a prefilter housing base 62 with a filter disc 64 inserted between the prefilter housing top and the prefilter housing base. Filter disc 64 may contain ultrafine charcoal to increase the vapor removal efficiency of the primary filter. Prefilter housing base 62 is attached to filter canister 106. The connection must be air tight such that no ambient air is allowed to enter the system at the connection in order to maintain maximum suction in the system.

The upper portion of filter canister 106 contains granular activated charcoal 108 which reacts with the laser plume to remove its toxic elements. After the laser plume flows through charcoal 108, it passes through an air flow stabilization chamber 110. Air flow stabilization chamber 110 aids in providing evenness of air flow through the filter and in reducing the amount of turbulence in the air. The length of air flow stabilization chamber 110 is altered to adjust the height of filter canister 106.

Finally, the laser plume is directed through a pleated filter 112 located in the lower portion of filter canister 106 which removes any remaining particulate debris contained in the air. Filter canister 106 is sealed around its bottom edge 114 to prevent ambient air from entering the system.

Figure 4:
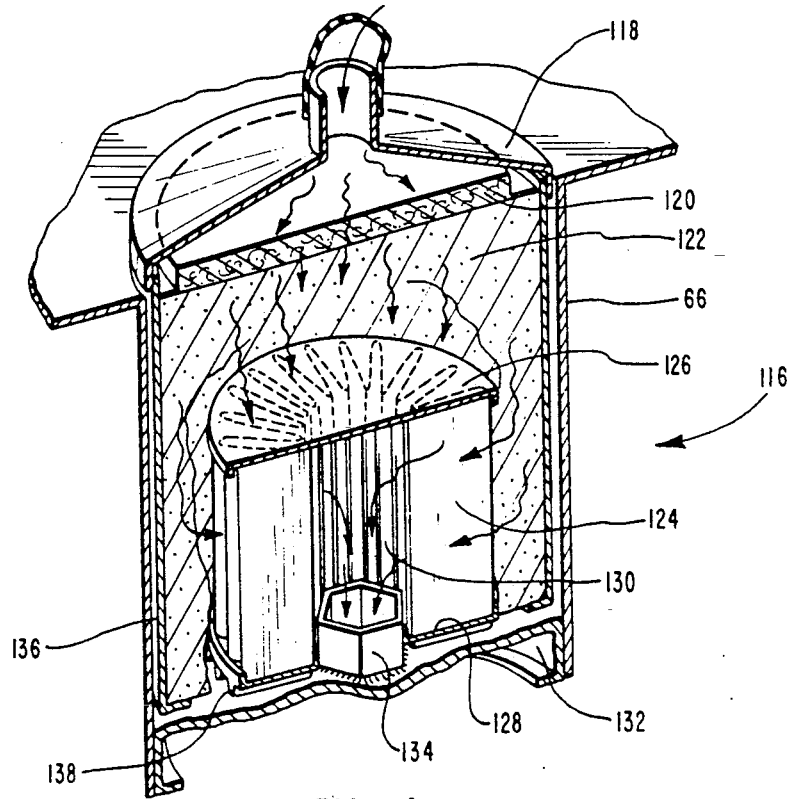
FIG. 4 is a cross-sectional perspective view of a second embodiment of a primary filter employed in the system shown in FIG. 1.

A second embodiment 116 of the primary filter is illustrated in FIG. 4 as being provided with a prefilter housing 118 which, in this embodiment of the present invention, is a vacuum-formed disposable cap which is permanently bonded to filter canister 106.

As with the first embodiment 104 of a primary filter illustrated in FIG. 3, prefilter housing 118 of second embodiment 116 of a primary filter also contains ultrafine charcoal impregnated discs 120 to assist in the filtering process. Prefilter housing 118 is attached directly to the filter canister and granular activated charcoal 122 is employed within filter canister 106 to detoxify the laser plume as it passes through primary filter 116.

A vertically pleated filter 124 having a cylindrical shape is preferably utilized within filter canister 106. Vertically pleated filter is made of glass fiber which facilitates the removal of very fine particulate matter. Because of the cylindrical geometry of the vertically pleated filter, substantially more filter surface area is exposed to the air traveling through the filter. This increases the filter efficiency and increases the life of the filter.

Vertically pleated filter 124 is sealed at its top with a cap 126, preferably made out of metal. At its base, the vertically pleated filter is sealed to filter canister 106 by a potting material 128, such as urethane. This ensures that all air passing through filter canister 106 will flow through, rather than around, the vertically pleated filter.

As the air exits the filter canister, it flows through a filter exhaust tunnel 130. The shape of filter exhaust tunnel 130 may be of a variety of geometric configurations such as the hexagonal shape illustrated in FIG. 4. A tunnel adaptor 132 is provided in the base of filter cylinder 66 to adapt this filter, having filter exhaust tunnel 132 to the system. A seal is provided around neck 134 of tunnel adaptor 132 to prevent cross-contamination of the filtered air with the ambient air.

Sidewall ribs 136 are provided both on the exterior of filter canister 106 and on the interior of filter cylinder 66. Likewise, base ribs 138 are provided on both the bottom of filter canister 106 and on tunnel adaptor 132 where the filter canister rests. Sidewall ribs 136 and base ribs 138 prevent a seal from forming between filter canister 106 and filter cylinder 66. By preventing the formation of such a seal, the primary filter may be easily removed when it is replaced.

Figure 5:
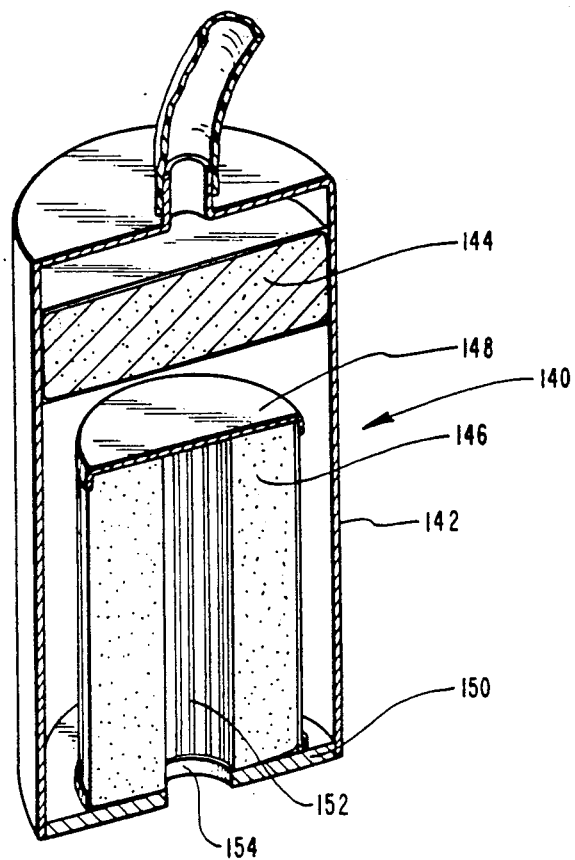
FIG. 5 is a cross-sectional perspective view of a third embodiment of a primary filter employed in the system shown in FIG. 1.

A third embodiment 140 of a primary filter which may be employed according to the present invention is illustrated in FIG. 5 as including within a filter canister 142 a segment of granular activated charcoal 144, similar to that configuration illustrated in FIG. 3 at 108. A vertically pleated filter 146 is mounted within filter canister 142. A cap 148 provides a seal at the top of vertically pleated filter 146 with a filter base 150 comprises of potting material, such as urethane, providing a seal for the bottom of vertically pleated filter 146. As with second embodiment 116 of a primary filter illustrated in FIG. 4, third embodiment 140 of FIG. 5 includes a filter exhaust tunnel 152 with a tunnel exhaust port 154 through which the air in the system may exit the primary filter.

Figure 6:
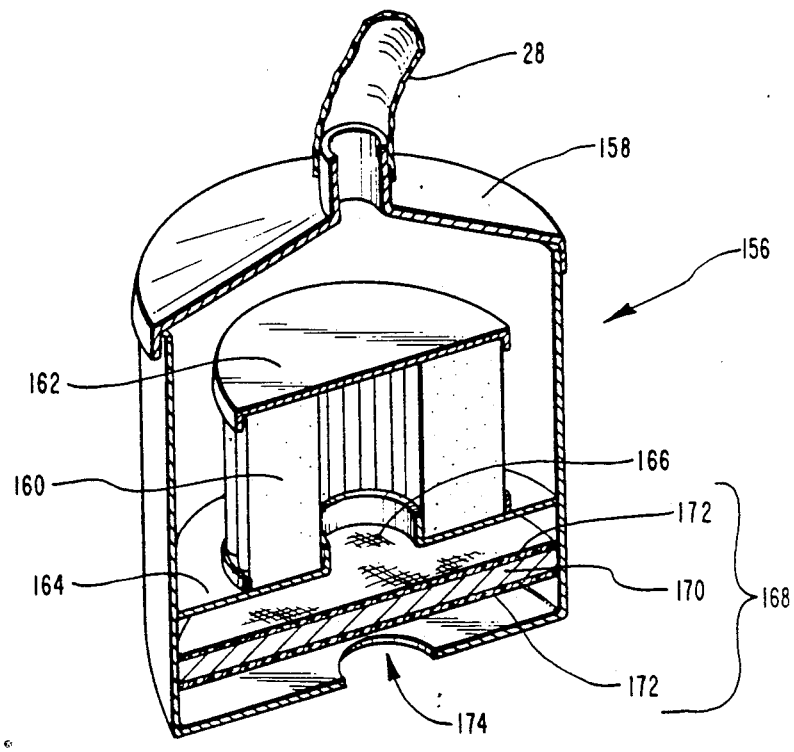
FIG. 6 is a cross-sectional perspective view of one embodiment of a disposable primary filter which may be used according to the present invention in the system shown in FIG. 1.

FIG. 6 illustrates a presently preferred embodiment of a single-use disposable filter 156 for use according to the present invention. The laser plume is introduced to filter 156 through inlet tube 28 which is attached to a filter lid 158. After entering filter 156, the plume then passes through a vertically pleated filter 160. Vertically pleated filter 160 includes a filter cap 162 which forces the plume to enter the filter through it sides.

Vertically pleated filter 160 is sealed around its base with a seal 164, so that the laser plume being filtered through the filter all exits the vertically pleated filter through an exhaust chamber 166 in the center of the base of the vertically pleated filter. Positioned beneath vertically pleated filter 160 within filter 156 is a charcoal filter 168. Charcoal filter 168 includes a center section of ultrafine charcoal 170 coated on each side with a carbonized covering 172.

After any particulate matter contained within the laser plume is filtered out by vertically pleated filter 160, any toxic elements within the laser plume are then removed by passing the plume through charcoal filter 168. The filtered air then exits the primary filter through a filter exhaust tunnel 174.

It will be appreciated that the filtering mechanism of the present invention may be embodied in a variety of configurations. For example, the present invention will work effectively using either a single-use, disposable filter or a reusable filter. Additionally, as can be observed by comparing the filters illustrated in FIGS. 5 and 6, that the filter may be configured with the paper filter above or below the charcoal filter without significantly affecting the effectiveness of the primary filter.

When using a disposable filter, such as that illustrated in FIG. 6, for some applications it may be desirable to mount the filter on the side of the housing. The filter could be provided with an inlet tube and an outlet tube attached to the filter and connected to the system.

Figure 7:
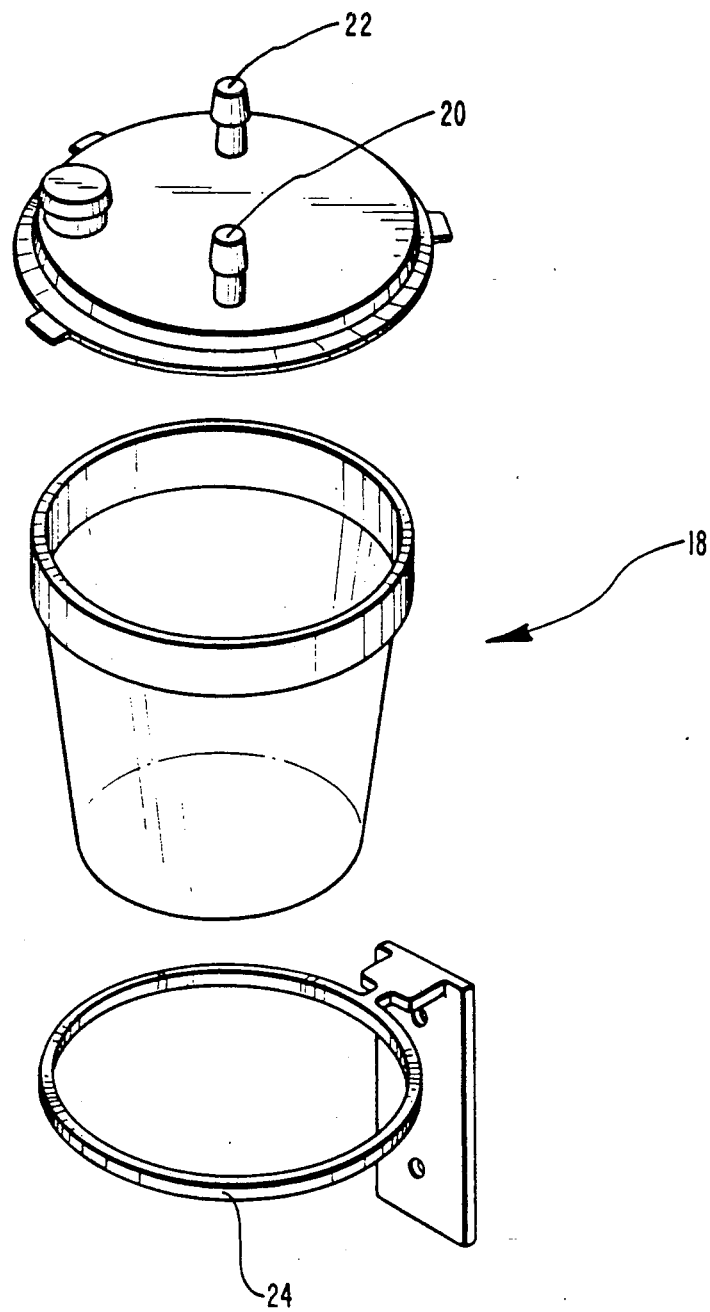
FIG. 7 is an exploded perspective view of the suction canister of the system of FIG. 1 of the present invention.

FIG. 7 illustrates suction canister 18 in an exploded perspective view. As explained previously, the suction canister is provided with both an inlet port 20 and an outlet port 22 and is utilized in closed surgical procedures for removing a liquid component from the laser plume. Suction canister 18 mounts to a sidewall of the system bottom housing 16 by means of a mounting ring 24. Alternatively, various other mounting methods, as are known in the art, may also be employed to accomplish this purpose. As the laser plume passes through the suction canister, any liquid component within the plume collects within the canister, as the flow of air through the canister is insufficient to carry the heavier liquid particles through the outlet port 22.

It will be appreciated that for open surgical procedures the present invention may be operated without using the suction canister 18. The use of suction canister 18 for closed procedures extends the life and improves the filtering efficiency of the primary filter by removing the liquid contained within the laser plume.

From the foregoing, it will be appreciated that the present invention provides an efficient and effective system for filtering laser plume from the surgical site.

The filters employed by the present invention are inexpensive, easy to replace, and provide maximum removal efficiency with extended life over filters found in systems of the prior art. The filters may be used in a disposable, sterile form or in a reusable form.

The air enhancement system of the present invention is self-contained, thereby eliminating the necessity to rely on hospital vacuum systems and reducing the risk of damaging such systems by introducing to them the particulate debris and other harmful elements unique to laser surgery. Also, due to the unique and advantageous configuration of the system, noise levels are kept to a minimum without reducing the amount of suction available to the system.

Figure 8:
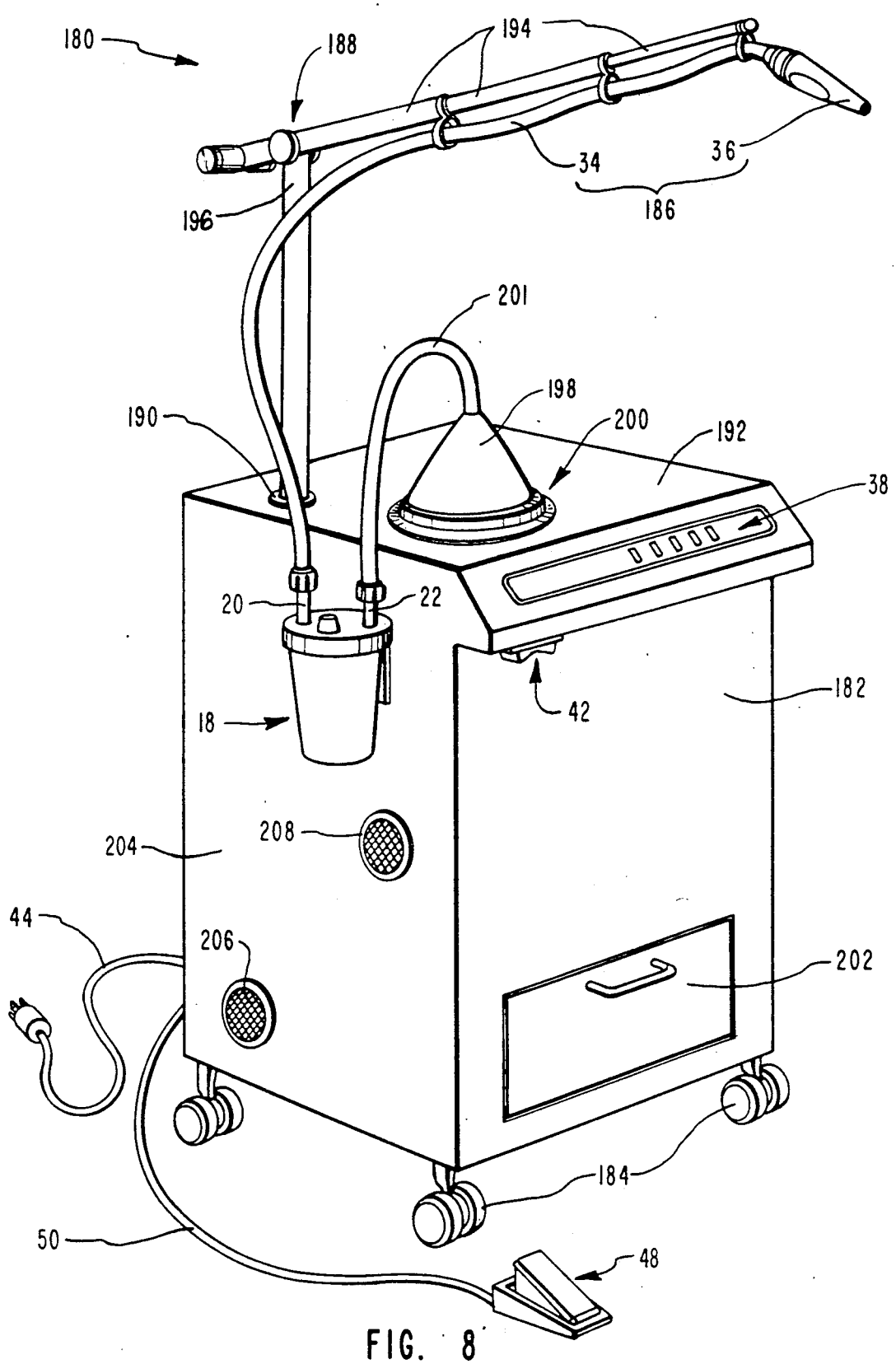
FIG. 8 is a perspective view of a second embodiment of a self-contained air enhancement system incorporating teachings of the present invention.

Shown in FIG. 8 is a second embodiment of a self-contained air enhancement system 180 for removing contaminants from a laser plume produced at a surgical site. The elements of system 180 are supported by a housing 182, which is mounted on rollers 184 for easy movement to the surgical site. As with system 110 illustrated in FIGS. 1 and 1A, system 180 includes a power cord 44, a foot switch cord 48 and a foot switch cord 50. Additionally visible on the exterior of housing 182 as shown in FIG. 8 are a control panel 38 by which to operate and regulate system 180, and a power switch 42.

For extracting the laser plume from the surgical site, system 180 includes a primary inlet tube 186 comprising a suction wand 36 and a suction wand leader tube 34. Primary inlet tube 186 is supportable at the surgical site by an articulated arm 188 which is rotatably mounted in a receptacle 190 in the top surface 192 of housing 182. Articulated arm 188 may take any number of forms, but is shown in FIG. 8 as comprising a plurality of telescoping sections 194 pivotable in a vertical plane from the top end of a support column 196. Support column 196 is rotatable in receptacle 190. In this manner suction wand 36 of primary inlet tube 186 can easily be oriented and extended to locate suction wand 36 within close proximity of the surgical site from which a laser plume is to be removed for treatment in system 180.

Such a laser plume passes through primary inlet tube 186 to inlet port 20 in the top of suction canister 18, which is mounted on the outside of housing 182. As has already been described in relation to system 110 shown in FIGS. 1 and 1A, the function of suction canister 18 is to remove liquid components of the contaminants from the laser plume being treated by system 180. Where liquid contaminants do not comprise a significant portion of such contaminants, it has already been mentioned that the inlet tube that extracts the laser plume from a surgical site, such as primary inlet tube 186, can bypass such a suction canister. In this case primary inlet tube 186 would be connected directly to the cap 198 of a primary filter canister 200 set into top surface 192 of housing 182. Doing so will obviate the need for secondary inlet tube 201 which is shown in FIG. 8 as interconnecting outlet port 22 of suction canister 18 with conical cap 198 of primary filter canister 200.

Figure 9:
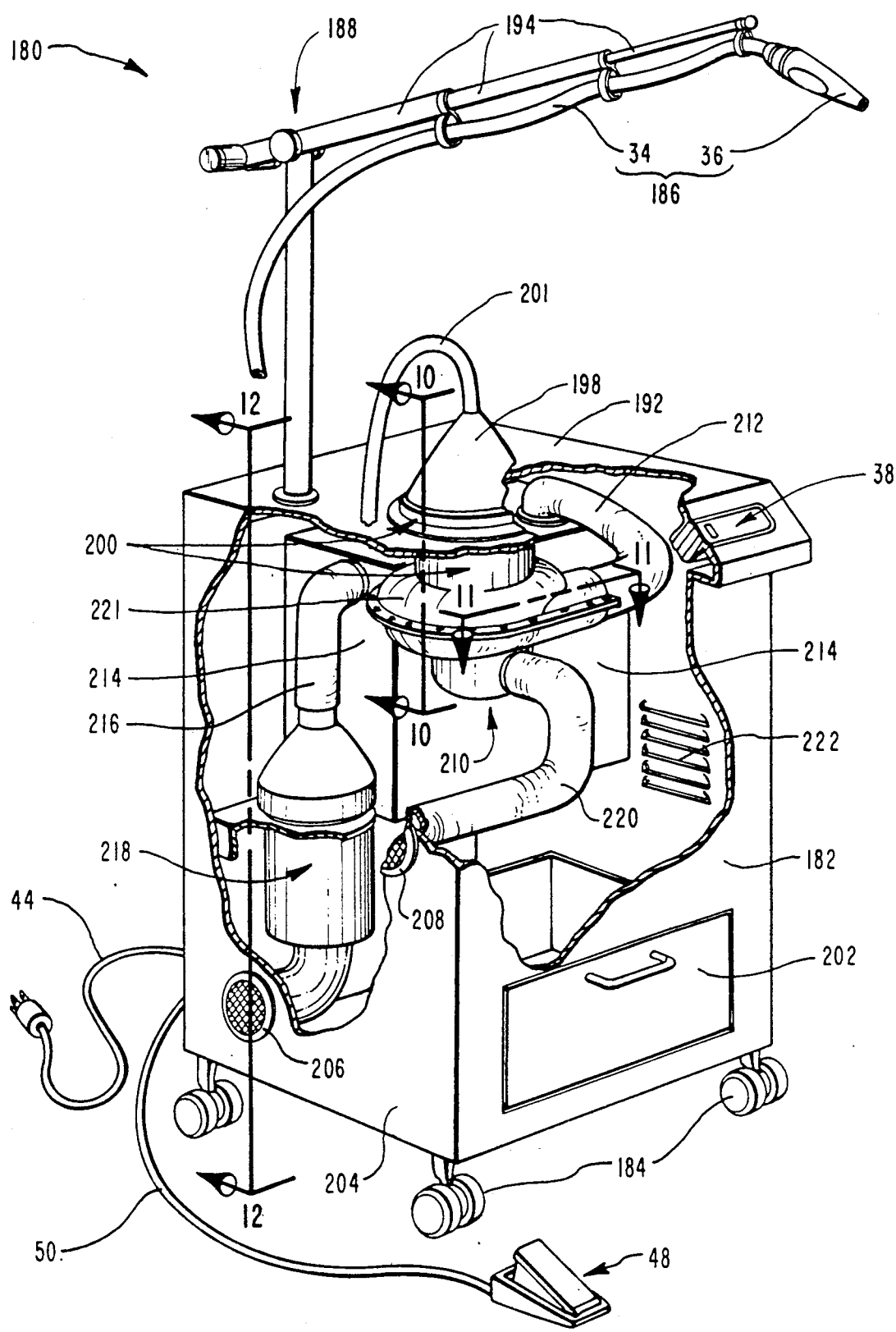
FIG. 9 is a perspective view of the system shown in FIG. 8 with the housing thereof partially broken away to disclose the constituent components located therein.

For the convenience of the personnel operating a system 180, the lower portion 204 of housing 182 includes a storage drawer 202. Formed through the side panel 200 of housing 182 is a treated air outlet 206 and a cooling air inlet 208. The function of these latter two structures will best be appreciated by reference to the view of system 180 shown in FIG. 9, where portions of housing 182 have been broken away to reveal components of system 180 interior to housing 182.

An overview of the steps of processing accorded to a laser plume within housing 182 of system 180 will be helpful to an understanding of the detailed description which will thereafter follow. Initially, the laser plume passes through primary inlet tube 186 and secondary inlet tube 201 to enter primary filter canister 200. This occurs under the influence of a fan 210 located therebelow. Fan 210 advances the laser plume for further treatment through a first hose 212 to a sterilization chamber 214. After treatment there, the laser plume moves through a second hose 216 and a secondary filter 218 for discharge through treated air outlet 206.

Fan 210 receives its own supply of cooling air through a cooling hose 220 that is connected to cooling air inlet 208. It should be noted, however, that the cooling air supplied through cooling hose 220 is prevented from cross-contamination with the laser plume being advanced by fan 210 through the provision of a fan housing 221 about the fan blades thereof. This and other structures shown externally in FIG. 9 will be explored in more detail in the subsequent FIGS. 10-12.

The cooling air about fan 210 does not accordingly pass through first hose 212 to sterilization chamber 214. Rather, that cooling air seeps out of fan 210 into the interior of housing 182 carrying heat from fan 210 which is then facilitated in escaping from housing 182 through louvers 222 to form in one of more walls thereof.

The path of a laser plume through system 180 thus includes in sequence primary inlet tube 186, suction canister 18, secondary inlet tube 201, primary filter canister 200, fan 210, sterilization chamber 214, and finally secondary filter 218. As used herein and in the claims which follow, the terms "upstream" and "downstream" relative to the elements of system 180 to refer to the sequence conventional laser plume passage therethrough just described.

Figure 10:
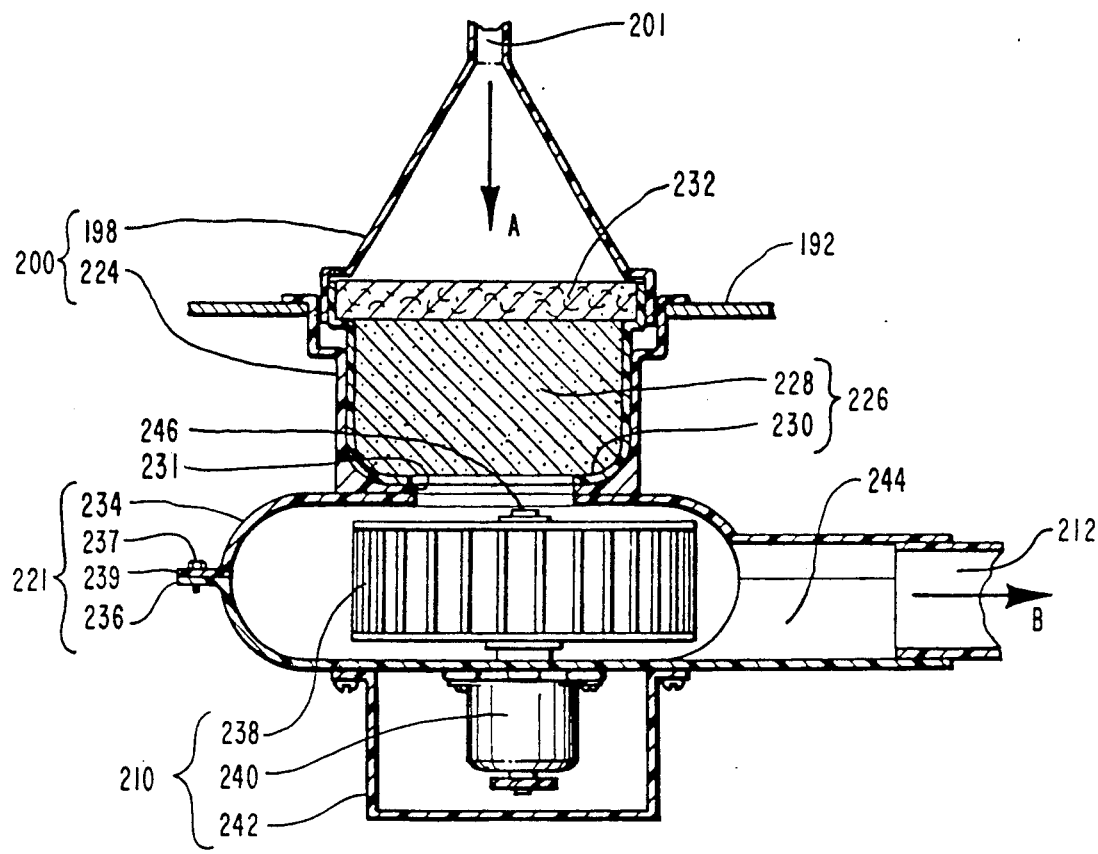
FIG. 10 is a cross-sectional elevation view of the primary filter and fan of the system shown in FIG. 9 taken along section line 10—10 therein.

As seen in FIG. 10, a laser plume in secondary inlet tube 201 enters the conical cap 198 of primary filter canister 200 in the direction shown by arrow A. The lower portion of primary filter canister 200 is a cylindrical enclosure 224 supported from top surface 192 of housing 182 so as to be substantially interior thereto. Within primary filter canister 200 is primary filter 226 which itself comprises a body of activated charcoal 228 held in a cup 230 which is removable from cylindrical enclosure 224 when conical cap 198 is opened. In this manner, when primary filter 226 becomes saturated with contaminants, it can easily be removed and replaced with another. Formed through the lower portion of cup 230 and cylindrical enclosure 224 is an aperture 231 which communicates with the interior of fan housing 221.

Also housed within primary filter canister 200 is a prefilter disc 232 which rests atop the body of activated charcoal 228. The function and structure of prefilter disc 232 is substantially similar to that of prefilter disc 64 shown in FIG. 3 and prefilter disc 120 shown in FIG. 4. Prefilter disc 232 can be removed from primary filter canister 210 independently of cup 230 with the body of activated charcoal 228 therein when conical cap 198 of primary filter canister 210 is removed from cylindrical enclosure 224. It is anticipated that the bulk of large particulate contaminants in the laser plume entering primary filter canister 210 in the direction shown by arrow A will be captured in prefilter disc 232. Accordingly, prefilter disc 232 is expected to be replaced for each surgical procedure with which system 180 is used, while the body of activated charcoal disposed in cup 230 will be replaced on a less frequent basis.

According to one aspect of the present invention, laser plume advancement means are provided located in housing 182 for inducing the laser plume to advance along its pathway through the system. This includes suction means located downstream on the pathway from the primary filter for advancing the laser plume along the pathway, ventilation means for supplying cooling air at ambient temperature to the suction means, and isolation means for preventing cross-contamination of the cooling air by the laser plume. As shown by way of example, and not limitation in FIG. 10 below primary filter canister 200 is a fan housing 221. Fan housing 221 comprises an upper fun housing section 234 and a lower fan housing section 236 secured one to another by a plurality of threaded bolts 237 which pass through apertures formed in peripheral flanges 239 on each of upper and lower fan housing sections 234, 236, respectively.

In one aspect of the present invention, the inner surface of fan housing 221 in a plane normal to the axes of rotation of fan blades 238 is provided in a preferred configuration which reduces the noise produced in system 180 and affords for the build up of pressure related to advancing the laser plume therethrough in an optimum fashion. Within fan housing 221 is mounted the rotating fan blade 238 that is driven in rotation by fan motor 240 directly therebelow. As understood and by reference to FIG. 10, fan motor 240 is enclosed within motor housing 242 into which the cooling air from cooling air hose 220 is supplied. Nevertheless, that cooling air is precluded from cross-contamination by the laser plume passing through fan housing 221 by maintaining fan housing 221 and all connections therewith along the path of the laser plume completely sealed from the interior of housing 182, as well as from the interior of motor housing 242. The laser plume treated in system 180 is drawn through inlet tube 186 and primary filter canister 220 into fan housing 221 by the rotating action of fan blades 238. This same rotating motion forces the laser plume from fan mousing 221 in the direction shown by arrow B by way of outlet throat 244 which is shown in FIG. 10 interconnected with first hose 212.

Figure 11:
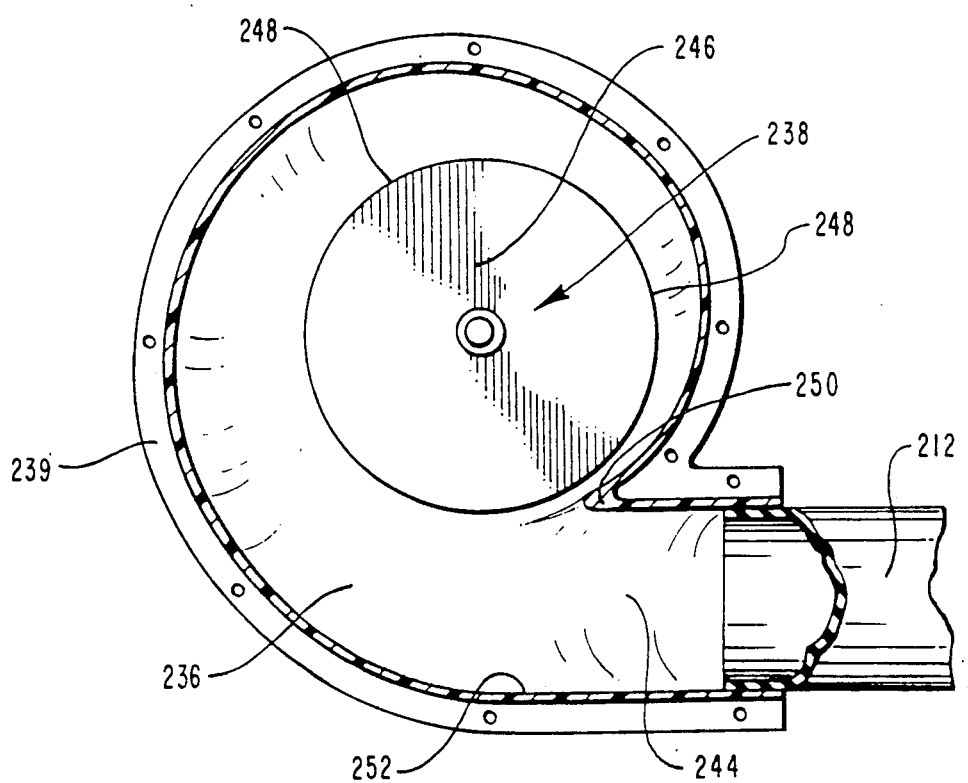
FIG. 11 is a cross-sectional plan view of the housing of the fan shown in FIG. 10 taken along section line 11—11 shown therein.

As shown in FIG. 11, this configuration assumes a spiral shape in relation to the axle 246 upon which fan blades 238 are mounted for rotation by motor 240. As shown in FIG. 11, the periphery 248 of fan blades 238 is closest to the wall of fan housing 221 at a point 250 at the beginning of outlet throat 244. Thereafter the opposed wall of fan housing 221 shown in FIG. 11 in the form of lower fan housing 236 recedes radially away from fan blade 238 in a circumferential direction away from point 250 toward the opposite side 252 of the beginning of outlet throat 244.

Figure 12:
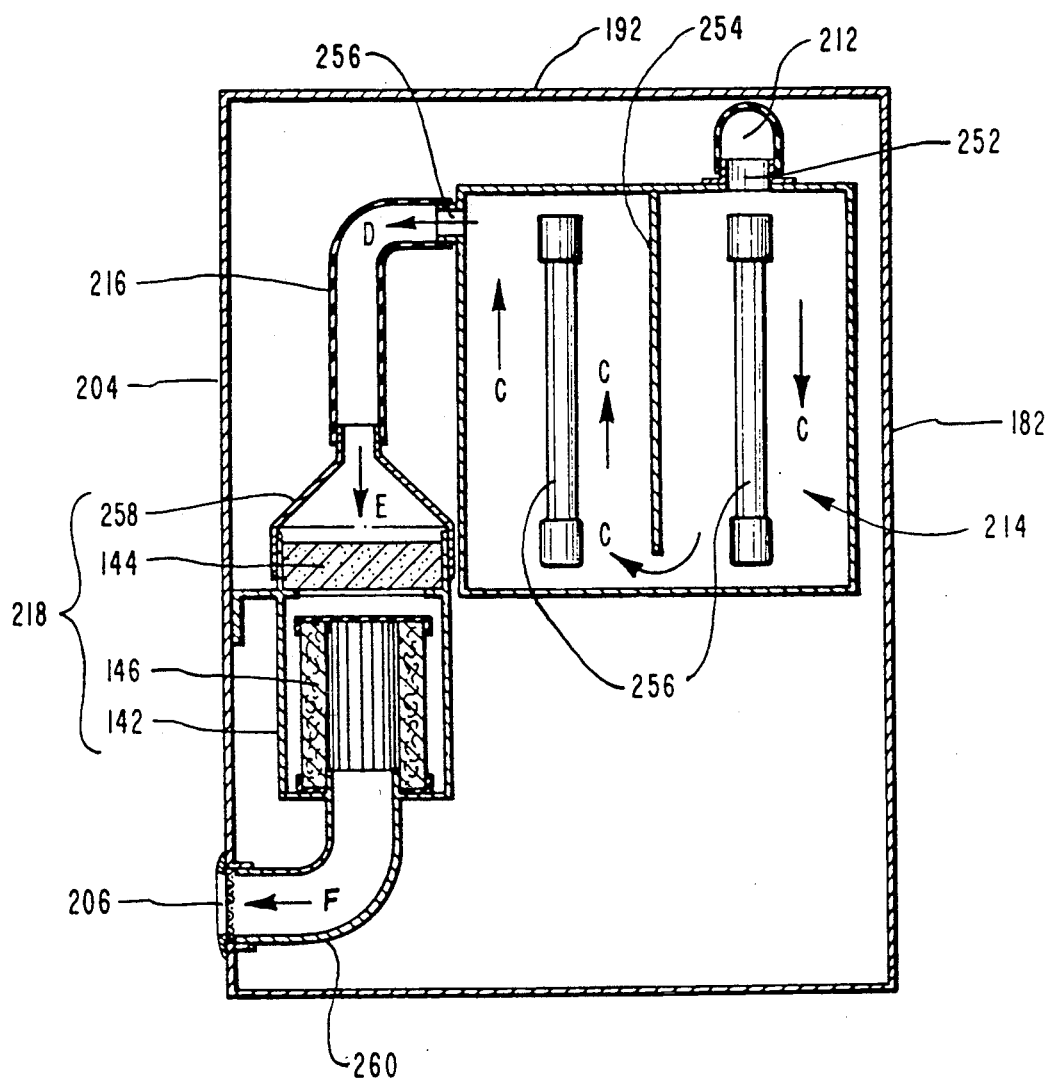
FIG. 12 is a cross-sectional elevation view of the system illustrated in FIG. 9 taken along section line 12—12 shown therein and illustrating in particular the internal constituents of the sterilization chamber of that system.

According to one aspect of the invention, sterilization means are disposed along the pathway of the laser plume through system 188 for killing biologically active material in the laser plume. As shown in FIG. 12, sterilization chamber 214 receives the laser plume through first hose 212 which is connected to inlet port 252 on the top and to one side of sterilization chamber 214. Therewithin a baffle 254 is disposed so as to cause the laser plume to travel through sterilization chamber 214 in a serpentine path as indicated by the arrows C. Mounted in sterilization chamber 214 parallel to the flow of the laser plume are a plurality of ultraviolet light tubes 256 which generate ultraviolet energy in sterilization chamber 214 in a range from about 1900 microwatts per square centimeter to about 6000 microwatts per square centimeter.

As indicated earlier, there is some suspicion that laser plumes of the type created during laser surgery may contain biologically viable materials, and that these materials could be harmful, if allowed to reenter the atmosphere of the surgical room in a viable form. It is the purpose of sterilization chamber 214 to reduce the risk from such potential biologically viable materials by killing any such material that passes along the path of the laser plume in system 180 as far as sterilization chamber 214. In one presently utilized embodiment of the inventive system, the sterilization chamber houses four ultraviolet bulbs 18 inches in length rated for 25 watts each. It is understood that while the doses of ultraviolet energy thus produced cannot be fully guaranteed to eliminate all biologically viable materials in the plume traveling the serpentine path indicated by arrow C, the treatment received in sterilization chamber 214 will reduce significantly the chances that such biologically viable material will emerge into the environment in which the surgery is occurring.

The laser plume exits sterilization chamber 214 in the direction shown by arrow D through outlet port 256 which is connected by way of second hose 216 to the conical cap 258 of a secondary filter 218. Secondary filter 218 resembles in most respects the structure of primary filter 140 shown in FIG. 5. Thus, as seen in FIG. 12, secondary filter comprises a vertically disposed pleated filter 146 and a layer of granular charcoal 144 to be disposed upstream from pleated filter 146. Both filtering elements are enclosed in the combination of filter canister 142 and conical cap 258. Ultimately clean air exits from secondary filter 218 through third hose 260 at treated air outlet 206 as shown by arrow F. The primary and secondary filters constitute a charcoal filter means located along the pathway of the laser plume for removing substantially all of the particulate contaminants and the odor from the laser plume. In this way treated air results which may be returned to the atmosphere of the operating room.

By contrast with system 10 shown in FIGS. 1 and 1A, system 180 sterilizes the laser plume being treated with ultraviolet light, thereby to further protect patients and personnel in the vicinity of the surgery being conducted. The housing used for the fan with which the laser plume is advanced through the system enhances its capacity to draw the laser plume from the surgery site and compel it through the treatment system. In addition the shape of the housing contributes to quiet operation.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A self-contained air enhancement system for removing contaminants from a laser plume produced at a surgical site, the system comprising:
   (a) a housing;
   (b) a primary inlet tube for extracting the laser plume from the surgical site;
   (c) a suction canister in communication with said inlet tube for removing liquid components of the contaminants from the laser plume;
   (d) a primary filter canister located in said housing and being in communication through a secondary inlet tube with said suction canister, said primary filter canister housing a primary filter for removing substantially all of the particulate contaminants and the odor from the laser plume;
   (e) suction means located downstream from said primary filter on the pathway of the laser plume through said system for advancing the laser plume in sequence through said primary inlet tube, said suction canister, said secondary inlet tube, and said primary filter canister;
   (f) ventilation means for supplying cooling air at ambient temperature to said suction means;
   (g) isolation means for preventing cross-contamination of said cooling air by the laser plume as the laser plume passes through said housing;
   (h) sterilization means disposed along said pathway for killing biologically active material in the laser plume; and
   (i) an outlet in said housing for expelling air from the laser plume treated by said system.

2. A system as recited in claim 1, wherein said primary filter is disposable.

3. A system as recited in claim 1, wherein said primary filter comprises a body of activated charcoal.

4. A system as recited in claim 1, wherein said suction canister is supported on the exterior of said housing.

5. A system as recited in claim 1, wherein said primary inlet tube has a smooth interior.

6. A system as recited in claim 1, wherein the free end of said primary inlet tube is supportable at the surgical site by an articulated arm mounted on said housing.

7. A system as recited in claim 1, further comprising a prefilter disc disposed in said primary filter canister upstream on said primary from said primary filter.

8. A system as recited in claim 1, wherein said sterilization means comprises a source of ultraviolet light.

9. A system as recited in claim 8, wherein the density of ultraviolet energy in said sterilization chamber is in the range from about 1,900 microwatts per square centimeter to about 6,000 microwatts per square centimeter.

10. A system as recited in claim 1, wherein said sterilization means comprises:
   (a) a sterilization chamber located along said pathway, said sterilization chamber having an inlet port for receiving the laser plume from said suction means and an outlet port for discharging the laser plume from said chamber;
   (b) a baffle disposed in said sterilization chamber to cause the laser plume to travel in a serpentine path through said sterilization chamber; and
   (c) an ultraviolet light tube disposed along said serpentine path.

11. A system as recited in claim 10, wherein a plurality of ultraviolet tubes are disposed along said serpentine path.

12. A system as recited in claim 1, wherein said suction means comprises a fan blade and an electric motor for driving said fan blade in rotation, and wherein said isolation means comprises a fan housing surrounding said fan blade for containing the laser plume.

13. A system as recited in claim 12, wherein the inner surface of said fan housing in a plane normal to the axis of said fan blade assumes a spiral configuration.

14. A system as recited in claim 1, further comprising a secondary filter located downstream from said suction means on said pathway.

15. A system as recited in claim 14, wherein said secondary filter contains activated charcoal.

16. A system as recited in claim 15, wherein said secondary filter further comprises a vertically disposed pleated filter having a cylindrical shape.

17. A system as recited in claim 1, further comprising indicator means for alerting a user of said system that said primary filter should be replaced.

18. A system as recited in claim 17, wherein said indicator means comprises:
(a) a pressure differential tube for measuring the pressure difference between ambient pressure and that generated by said suction means; and
(b) an indicator means for alerting a user when said pressure difference exceeds a predetermined threshold.

19. A system as recited in claim 1, wherein said suction canister is provided with an inlet port and an outlet port on the top thereof, said inlet port being connected to said primary inlet tube.

20. A system as recited in claim 19, wherein said outlet port of said suction canister is in communication with said primary filter.

21. A system as recited in claim 20, wherein said inlet port and said outlet port of said suction canister have inside diameters of different sizes.

22. A system as recited in claim 21, wherein said inlet port of said suction canister has an inside diameter that is smaller than the inside diameter of said outlet port of said suction chamber.

23. A system as recited in claim 22, wherein said inlet port of said suction canister has an inside diameter that is smaller than the inside diameter of said primary inlet tube.

24. A system as recited in claim 1, wherein said secondary inlet tube has in inside diameter in the range of from about 1.00 inches to about 1.75 inches.

25. A system as recited in claim 24, wherein said secondary inlet tube has an inside diameter in the range of from about 1.15 inches to about 1.50 inches.

26. A system as recited in claim 25, wherein said secondary inlet tube has an inside diameter in the range of from about 1.25 inches to about 1.345 inches.

27. A self-contained air enhancement system wherein a laser plume produced by a laser at a surgical site is drawn along a pathway through the system to remove contaminants therefrom, said system comprising:
(a) a housing for supporting the elements of said system;
(b) a primary inlet tube for extracting the laser plume from the surgical site;
(c) a suction chamber communicating with said primary inlet tube for removing liquid components of the laser plume;
(d) charcoal filter means located along the pathway for removing substantially all of the particulate contaminants and the odor from the laser plume;
(e) laser plume advancement means located in said housing for inducing the laser plume to advance along the pathway; and
(f) sterilization means located along the path for killing biologically active material in the laser plume.

28. A system as recited in claim 27, wherein said sterilization means comprises a source of ultraviolet light disposed along said pathway.

29. A system as recited in claim 27, wherein said suction chamber is supported by said housing, and wherein said suction canister is provided with an inlet port and an outlet port on the top thereof, said inlet port being connected to said inlet tube.

30. A system as recited in claim 27, further comprising tube reduction means for connecting a first portion of said inlet tube remote from said laser plume advancement means to a second portion of said inlet tube located between said first portion thereof and said laser plume advancement means, said first portion of said inlet tube having a smaller inner diameter than the inner diameter of said second portion of said inlet tube, thereby increasing the suction capabilities of said laser plume advancement means.

31. A system as recited in claim 27, further comprising a control panel for permitting a user of said system to regulate the degree of suction provided thereby at the surgical site.

32. A system as recited in claim 27, wherein said sterilization means comprises:
(a) a sterilization chamber located along said pathway;
(b) a baffle disposed in said sterilization chamber so as to cause the laser plume to travel in a serpentine path through said sterilization chamber; and
(c) an ultraviolet light tube disposed along said serpentine path.

33. A system as recited in claim 32, wherein said sterilization chamber is located on said pathway downstream from said laser plume advancement means.

34. A system as recited in claim 32, wherein a plurality of ultraviolet tubes are disposed along said serpentine path.

35. A system as recited in claim 27, wherein said charcoal filter means comprises:
(a) a primary filter located on said pathway between said primary inlet tube and the laser plume advancement means; and
(b) a secondary filter located on said pathway on the opposite side of said laser plume advancement means from said primary filter.

36. A system as recited in claim 35, wherein said primary filter is disposable and comprises a body of activated charcoal.

37. A system as recited in claim 36, wherein said activated charcoal comprises ultrafine charcoal impregnated discs.

38. A system as recited in claim 35 further comprising a prefilter disc located on the pathway adjacent to and upstream of said primary filter.

39. A system as recited in claim 35, wherein said secondary filter comprises:
(a) a vertically disposed pleated filter having a cylindrical shape; and
(b) a layer of activated charcoal located on the pathway between said pleated filter and said laser plume advancement means.

40. A system as recited in claim 39, wherein said activated charcoal comprises ultrafine charcoal impregnated discs.

41. A system as recited in claim 35, wherein said laser plume advancement means comprises:
(a) suction means for advancing the laser plume along the pathway, said suction means being located downstream on the pathway from said primary filter;
(b) ventilation means for supplying cooling air at ambient temperature to said suction means; and
(c) isolation means for preventing cross-contamination of said cooling air by the laser plume as the laser plume passes along the pathway.

42. A system as recited in claim 41, wherein said suction means comprises a fan blade and an electric motor for driving said fan blade in rotation, and wherein said ventilation means supplies ambient air from the exterior of said housing to said electric motor.

43. A system as recited in claim 42, wherein said isolation means comprises a fan housing surrounding said fan blade for containing the laser plume, the inner surface of said fan housing in a plane normal to the axis of the fan blade assuming a spiral configuration.

44. A system as recited in claim 35, wherein said primary filter is disposable.

45. A self-contained air enhancement system wherein a laser plume produced by a laser at a surgical site is drawn along a pathway through the system to remove contaminants therefrom, said system comprising:

(a) a housing for supporting the elements of said systems;

(b) a primary inlet tube for extracting the laser plume from the surgical site;

(c) a suction canister in communication with said inlet tube for removing liquid components of the contaminants of the laser plume, said suction canister being provided with an inlet port and an outlet port on the top thereof, said inlet port being connected to said primary inlet tube;

(d) a primary filter canister located in said housing and being in communication through a secondary inlet tube with said outlet port of said suction canister, said primary filter canister housing a primary filter for removing substantially all of the particulate components and the odor from said laser plume and a prefilter disk disposed in said primary filter canister upstream of said primary filter on the pathway;

(e) a fan blade located downstream of said primary filter canister on the pathway for advancing the laser plume through said system;

(f) a fan housing surrounding said fan blade for containing the laser plume, the inner surface of said fan housing in a plane normal to the access of said fan blade assuming a spiral configuration;

(g) an electric motor for driving said fan blade in rotation;

(h) ventilation means for supplying cooling air from the outside of said housing to said electric motor while said fan housing prevents cross-contamination of said cooling air by the laser plume;

(i) a sterilization chamber located along said pathway downstream from said fan blade;

(j) a baffle disposed in said sterilization chamber so as to cause the laser plume to travel in a serpentine path through said sterilization chamber;

(k) an ultraviolet light tube disposed along said serpentine path;

(l) a secondary filter located on said pathway downstream from said sterilization chamber, said secondary filter comprising:
  (i) a vertically disposed pleated filter having a cylindrical shape; and
  (ii) a layer of activated charcoal located on the pathway between said pleated filter and said sterilization chamber; and (m) an outlet in said housing communicating with said secondary filter through which to expel air from the laser plume treated by said system.

46. A method for the efficient removal of contaminants in a laser plume produced at a surgical site, said method comprising the steps:

(a) aspirating the laser plume from the surgical site;

(b) removing liquid contaminants from the laser plume;

(c) filtering substantially all particulate contaminants and the odor from the laser plume;

(d) sterilizing the laser plume to kill substantially all biologically active material; and (e) expelling the treated laser plume into the atmosphere.

47. A method as recited in claim 46, wherein said step of filtering comprises the steps:

(a) advancing the laser plume through a primary charcoal filter immediately after said step of removing liquid contaminants; and (b) passing the laser plume through a secondary charcoal filter immediately after said step of sterilizing the laser plume.

48. A method as recited in claim 46, wherein said step of removing liquid contaminants comprises the steps of directing the plume through a suction canister from said inlet port to said outlet port thereof.

49. A method as recited in claim 46, wherein said step of sterilizing the laser plume comprises the steps:

(a) driving the laser plume in a serpentine line of travel through a sterilization housing; and (b) exposing the laser plume to ultraviolet radiation as the laser plume is driven in said serpentine line of travel.

* * * * *

UNITED STATES PATENT AND TRADEMARK OFFICE
CERTIFICATE OF CORRECTION

Page 1 of 2

PATENT NO. : 5,047,072

DATED : September 10, 1991

INVENTOR(S) : THOMAS J. WERTZ et al.

It is certified that error appears in the above-identified patent and that said Letters Patent is hereby corrected as shown below:

Column 2, line 7, "biological" should be --biologically--
Column 2, line 47, "in to" should be --into--
Column 4, line 27, "when interior" should be --when the interior--
Column 4, line 38, after "therethrough" insert --.--
Column 5, lines 17-18, "particular contaminants" should be --particulate contaminants--
Column 5, line 44, after "drawings" insert --.--
Column 8, line 48, after "and" insert --may--
Column 8, line 55, before "are" insert --For closed procedures, the smoke and debris of the laser plume--
Column 9, line 52, "air tight" should be --airtight--
Column 10, lines 58-59, "comprises" should be --comprised--
Column 11, line 5, "it sides" should be --its sides--
Column 13, line 15, delete "to form" and insert therefor --formed--
Column 13, line 23, delete second occurrence of "to"
Column 13, line 60, after "provided" insert --and are--
Column 14, line 1, delete ","
Column 14, line 1, after "below" insert --,--
Column 14, line 3, "fun" should be --fan--
Column 14, line 12, delete "for"
Column 14, line 12, "build up of pressure" should be --build-up of pressure--
Column 15, line 3, after "bulbs" insert --which are--
Column 15, line 3, after "length" insert --and which are--
Column 15, line 18, "secondary filter" should be --secondary filter 218--

UNITED STATES PATENT AND TRADEMARK OFFICE
CERTIFICATE OF CORRECTION

PATENT NO. : 5,047,072

DATED : September 10, 1991

INVENTOR(S) : THOMAS J. WERTZ et al.

It is certified that error appears in the above-identified patent and that said Letters Patent is hereby corrected as shown below:

Column 17, line 44, delete "suction chamber" and insert therefor --suction canister--
Column 17, line 22, delete "suction chamber" and insert therefor --suction canister--
Column 17, line 59, delete "suction chamber" and insert therefor --suction canister--

Signed and Sealed this

Eighth Day of June, 1993

Attest:

*Attesting Officer*

MICHAEL K. KIRK

*Acting Commissioner of Patents and Trademarks*